United States Patent
Choi

(10) Patent No.: US 11,278,746 B2
(45) Date of Patent: Mar. 22, 2022

(54) LOCALIZED FAT DESTROYING METHOD AND HYPOTONIC SOLUTION FOR DESTROYING LOCALIZED FAT

(71) Applicant: MyoungSeok Choi, Seoul (KR)

(72) Inventor: MyoungSeok Choi, Seoul (KR)

( * ) Notice: Subject to any disclaimer, the term of this patent is extended or adjusted under 35 U.S.C. 154(b) by 444 days.

(21) Appl. No.: 16/515,047

(22) Filed: Jul. 18, 2019

(65) Prior Publication Data
US 2020/0376302 A1    Dec. 3, 2020

(30) Foreign Application Priority Data
May 31, 2019    (KR) .......................... 10-2019-0064371

(51) Int. Cl.
*A61N 7/00*    (2006.01)
*A61K 8/49*    (2006.01)
*A61K 8/67*    (2006.01)

(52) U.S. Cl.
CPC .............. *A61N 7/00* (2013.01); *A61K 8/4953* (2013.01); *A61K 8/676* (2013.01); *A61N 2007/0008* (2013.01)

(58) Field of Classification Search
CPC .... A61N 7/00; A61N 2007/0008; A61N 7/02; A61N 2007/025; A61K 8/4953; A61K 8/676; A61K 8/41; A61K 8/42; A61K 8/4926; A61K 2800/91; A61K 8/66; A61K 9/08; A61K 47/02; A61K 47/22; A61K 9/0021; A61K 41/0023; A61K 8/9771; A61K 9/0004; A61K 31/375; A61K 31/522; A61K 36/16; A61K 2800/82; A61P 41/00; A61P 3/04; A61Q 19/06; A61Q 19/00; A61M 5/3298
See application file for complete search history.

(56) References Cited

U.S. PATENT DOCUMENTS

| | | | | |
|---|---|---|---|---|
| 5,049,440 A | * | 9/1991 | Bornhoeft, III | ......... A61K 8/36 442/123 |
| 2007/0060989 A1 | * | 3/2007 | Deem | ................ A61B 18/1477 607/99 |
| 2010/0087550 A1 | * | 4/2010 | Marlowe | ................ A61P 27/00 514/781 |

* cited by examiner

*Primary Examiner* — Hien N Nguyen
(74) *Attorney, Agent, or Firm* — Revolution IP, PLLC

(57) ABSTRACT

A local fat destroying method of the present invention includes: preparing a hypotonic solution; injecting the hypotonic solution into a local fat tissue using a multi-needle; expanding the fat cells while the hypotonic solution injected into the fat tissue is injected into the fat cells by an osmotic pressure phenomenon; and destroying the expanded fat cells by ultrasonic waves by applying the ultrasonic waves to the fat tissue.

4 Claims, 4 Drawing Sheets

[FIG. 1]
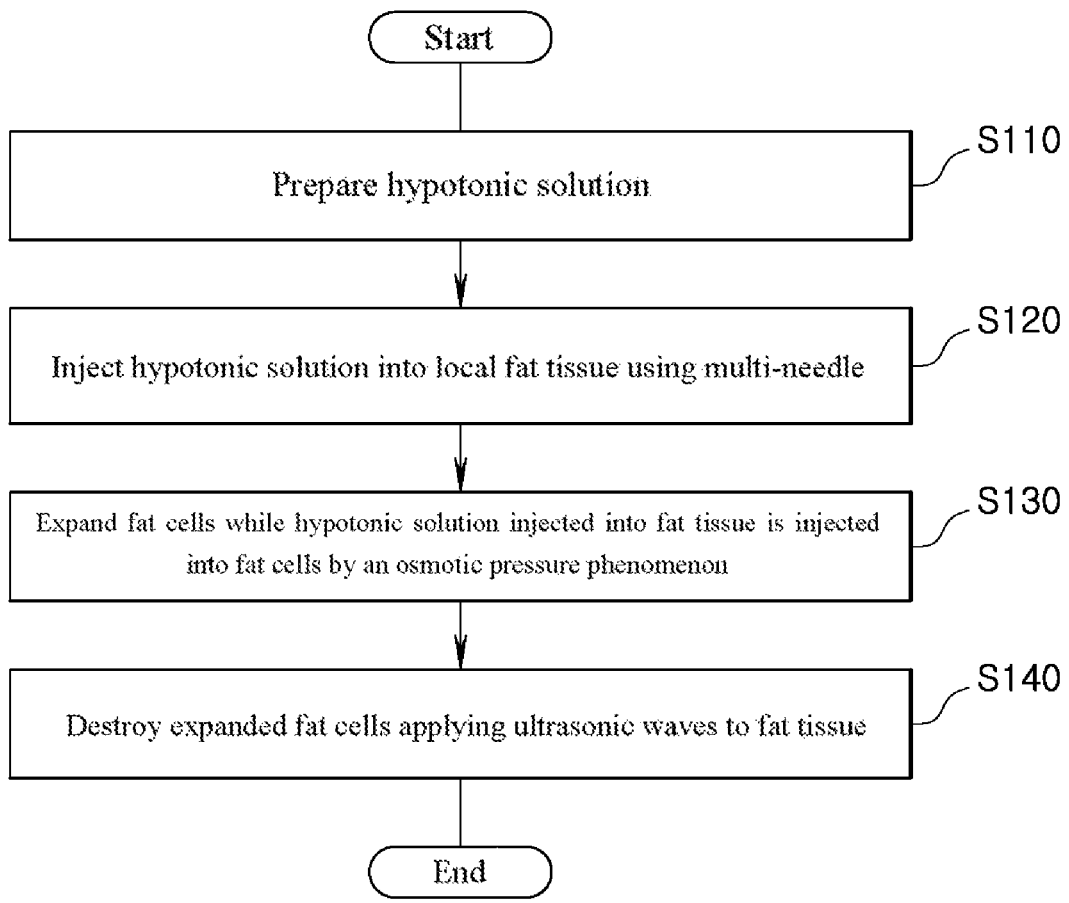

[FIG. 2]
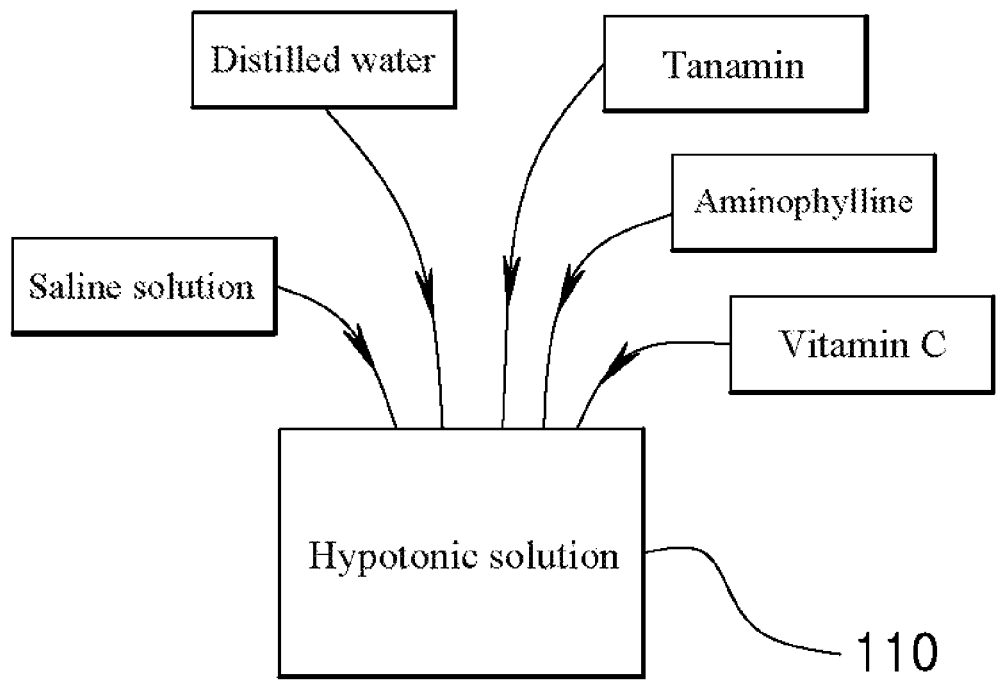
[FIG. 3]
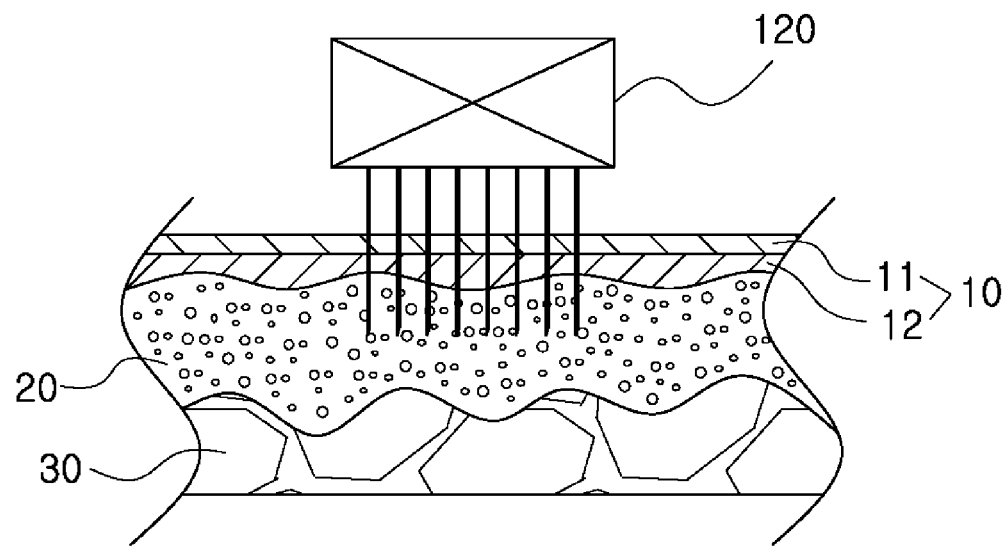

[FIG. 4]
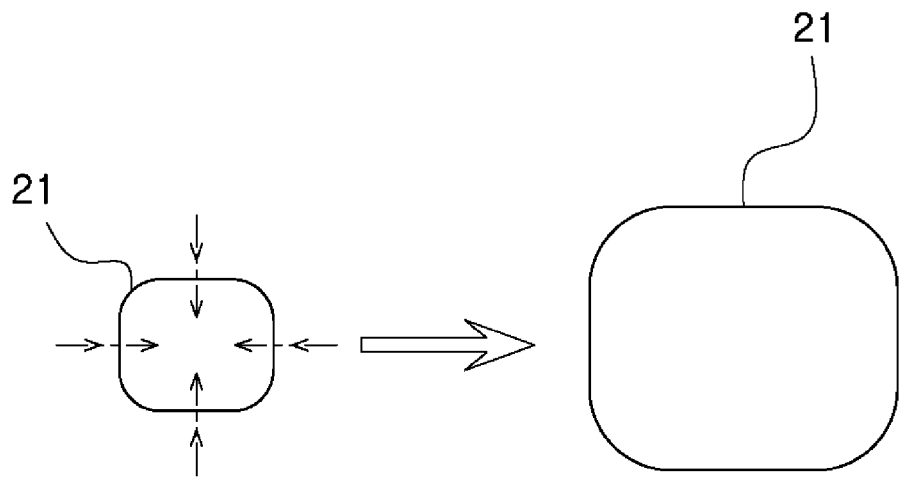
[FIG. 5]
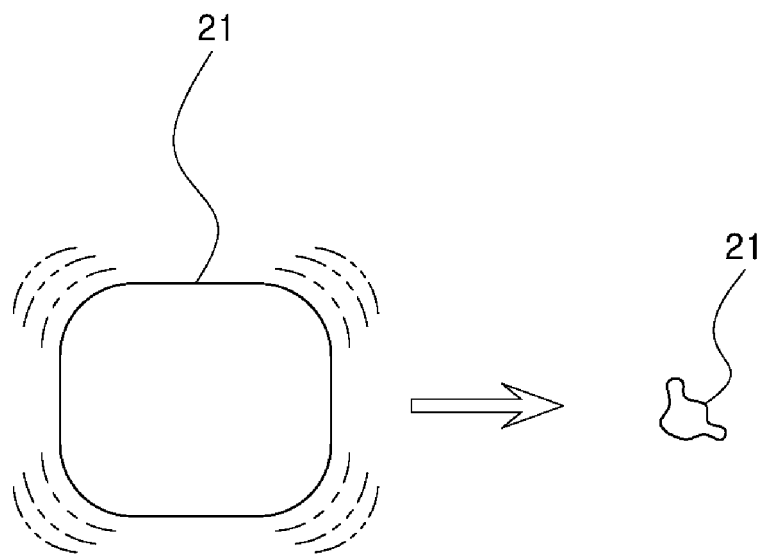

[FIG. 6]
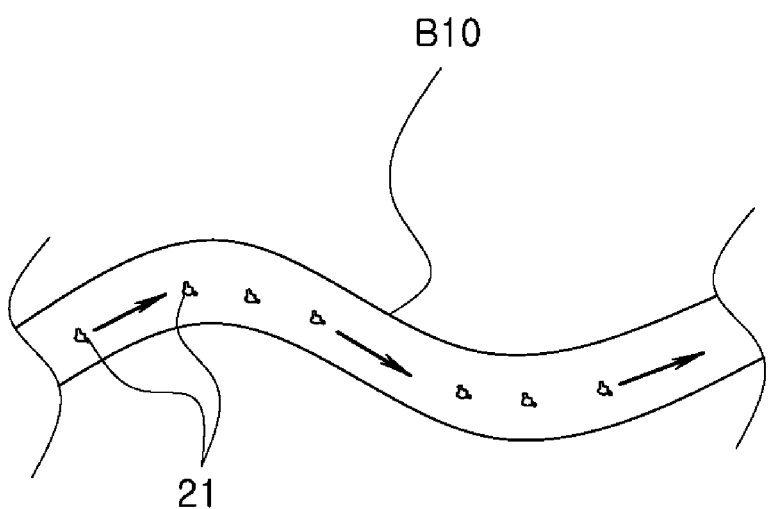

LOCALIZED FAT DESTROYING METHOD AND HYPOTONIC SOLUTION FOR DESTROYING LOCALIZED FAT

TECHNICAL FIELD

The present invention relates to a localized fat destroying technique.

BACKGROUND ART

In general, obesity is known to be the cause of all diseases. There are many causes of the obesity, but the most significant factor is the excess fat accumulated in the body. As this fat becomes obesity, the fat collects in the liver, blood vessels, and blood, resulting in symptoms such as fatty liver, arteriosclerosis, and hyperlipemia. Furthermore, the obesity is not apparently good, and social phobia and the like may occur.

There are various dieting methods and surgical treatment methods such as surgery to alleviate the obesity. However, dieting is not easy to succeed, and surgical methods are risky.

As a non-invasive method to reduce subcutaneous fat layers or fat tissues introduced up to now, there is cryolipolysis which induces fat cells to become spontaneous necrosis by a principle of selectively destroying only fat cells without damaging tissues such as epidermis and nerves through direct cooling, that is, an apoptosis principle.

However, in such cryolipolysis may, there is a problem that side effects such as frostbite or necrosis occur by cooling to the skin of the treatment site as well as the subcutaneous fat at about −9° C.

DISCLOSURE

Technical Problem

An object of the present invention is to provide a localized fat destroying method and a hypotonic solution for destroying localized fat capable of destroying the localized fat by a non-invasive method without damage to the skin such as frostbite.

Technical Solution

In order to achieve the object, according to an embodiment of the present invention, the local fat destroying method of the present invention includes: preparing a hypotonic solution; injecting the hypotonic solution into a local fat tissue using a multi-needle; expanding the fat cells while the hypotonic solution injected into the fat tissue is injected into the fat cells by an osmotic pressure phenomenon; and destroying the expanded fat cells by ultrasonic waves by applying the ultrasonic waves to the fat tissue.

The destroying of the expanded fat cells by ultrasonic waves may include: destroying the expanded fat cells or inducing the destruction thereof by applying an impact caused by resonance to the expanded fat cells; and destroying or dissolving the fat cells by applying high-intensity focused ultrasonic waves to the fat cells applied with the impact caused by resonance.

The preparing of the hypotonic solution may include: preparing a saline solution which is a 0.9% NaCl solution equal to an isotonic solution; and adding distilled water so that the prepared saline solution is a 0.3 to 0.4% NaCl solution.

The preparing of the hypotonic solution may further include adding tanamin, which promotes blood and lymphatic circulation, aminophylline, which promotes lipolysis, and vitamin C that increases collagen synthesis to the saline solution.

The localized fat destroying method according to the embodiment of the present invention may further include smoothly discharging the fat cells destroyed with ultrasonic waves through blood vessels without the coagulation due to the reaction of the tanamin and the aminophylline; and increasing the elasticity of the skin sagged by the destruction of the fat cells by the action of vitamin C.

In the destroying or dissolving of the fat cells by applying the high-intensity focused ultrasonic waves, the elasticity of the skin may be increased while the skin dermal layer is stimulated by the heat effect of the high-intensity focused ultrasonic waves.

In the preparing of the hypotonic solution, the hypotonic solution may comprise 53 to 63 wt % of distilled water, 2 to 3 wt % of aminophylline, 1 to 2 wt % of tanamin, 0.3 to 0.5 wt % of vitamin C, and a remaining content of a saline solution based on the weight ratio of the total composition.

The hypotonic solution may further include 1 to 3 wt % of a local anesthetic agent, lidocain based on the weight ratio of the total composition.

The hypotonic solution may further include hyaluronidase in units of 1500IU.

According to another embodiment of the present invention, a hypotonic solution for removing localized fat may comprise 53 to 63 wt % of distilled water, 2 to 3 wt % of aminophylline, 1 to 2 wt % of tanamin, 0.3 to 0.5 wt % of vitamin C, 1 to 3 wt % of a local anesthetic agent, lidocain, and a remaining content of a saline solution based on the weight ratio of the total composition.

The hypotonic solution for removing localized fat according to another embodiment of the present invention may further include 1 to 3 wt % of a local anesthetic agent, lidocain based on the weight ratio of the total composition.

The hypotonic solution for removing localized fat according to another embodiment of the present invention may further include hyaluronidase in units of 1500 IU.

Advantageous Effects

As described above, the localized fat destroying method according to the exemplary embodiment of the present invention may have the following effects.

According to the embodiment of the present invention, there is provided a technical configuration including preparing a hypotonic solution, injecting the hypotonic solution into a local fat tissue using a multi-needle, expanding the fat cells while the hypotonic solution injected into the fat tissue is injected into the fat cells by an osmotic pressure phenomenon, and destroying the expanded fat cells by ultrasonic waves by applying the ultrasonic waves to the fat tissue, and thus while the fat cells are expanded by an osmotic pressure phenomenon of the hypotonic solution injected into the fat tissue through the multi-needle, the expanded fat cells may be destroyed by applying ultrasonic waves. Therefore, it is possible to easily destroying localized fat without damage to the skin such as frostbite by a non-invasive method and particularly, when ultrasonic waves are applied to the fat cells expanded by the hypotonic solution, the propagation speed is increased by about 3 times as compared with when the ultrasonic waves are not applied, and thus it is possible to improve greatly destruction efficiency of the fat cells.

Further, according to the embodiment of the present invention, there is provided a technical configuration in which the destroying of the expanded fat cells by ultrasonic waves includes destroying the expanded fat cells or inducing the destruction thereof by applying an impact caused by resonance to the expanded fat cells and destroying or dissolving the fat cells by applying high-intensity focused ultrasonic waves to the fat cells applied with the impact caused by resonance. Accordingly, while a resonance effect is generated by the excitation of the ultrasonic waves oscillated in a cavitation ultrasound device, the fat cells may be burst and destroyed by the impact caused by the resonance. In addition, in the high-intensity focused ultrasound device, while high heat is generated by the high-intensity focused ultrasound wave oscillated with the precise focus from the fat cells as a target, the membranes of the fat cells may be burst and destroyed or the fat cells may be physically dissolved and destroyed by high heat. In addition, the elasticity of the skin may be increased while the skin dermal layer is stimulated by the heat effect of the high-intensity focused ultrasonic waves.

Further, according to the embodiment of the present invention, there is provided a technical configuration in which the preparing of the hypotonic solution includes preparing a saline solution which is a 0.9% NaCl solution equal to an isotonic solution and adding distilled water so that the prepared saline solution is a 0.3 to 0.4% NaCl solution. For reference, as a result of animal experiments, it is confirmed that when the NaCl solution of the hypotonic solution is less than 0.3%, the osmotic pressure phenomenon occurs extremely, and thus there are side effects such as expansion of the skin tissue as well as the fat cells, and it is confirmed that when the NaCl solution exceeds 0.4%, the occurrence degree of the osmotic pressure phenomenon is remarkably reduced.

Further, according to the embodiment of the present invention, there is provided a technical configuration in which the preparing of the hypotonic solution further includes adding tanamin, which promotes blood and lymphatic circulation, aminophylline, which promotes lipolysis, and vitamin C that increases collagen synthesis to the saline solution. Accordingly, the fat cells destroyed with ultrasonic waves may be smoothly discharged through blood vessels (that is, discharged by kidney and urine) without the coagulation due to the reaction of the tanamin and the aminophylline and at the same time, the elasticity of the skin sagged by the destruction of the fat cells may be increased by the action of vitamin C.

DESCRIPTION OF DRAWINGS

FIG. 1 is a flowchart schematically illustrating a localized fat destroying method according to an exemplary embodiment of the present invention.

FIG. 2 is a view schematically illustrating a process of preparing a hypotonic solution.

FIG. 3 is a view schematically illustrating a process of injecting the hypotonic solution by a multi-needle.

FIG. 4 is a view schematically illustrating a process of expanding fat cells by osmotic pressure of the hypotonic solution.

FIG. 5 is a view schematically illustrating a process of destroying fat cells by ultrasonic waves.

FIG. 6 is a view schematically illustrating a process of discharging destroyed fat cells through blood vessels.

MODES OF THE INVENTION

Hereinafter, embodiments of the present invention will be described in detail with reference to the accompanying drawings so as to easily implement those with ordinary skill in the art to which the present invention pertains. However, the present invention may be embodied in many different forms and are limited to embodiments described herein.

FIG. 1 is a flowchart schematically illustrating a localized fat destroying method according to an exemplary embodiment of the present invention. FIG. 2 is a view schematically illustrating a process of preparing a hypotonic solution, FIG. 3 is a view schematically illustrating a process of injecting the hypotonic solution by a multi-needle, FIG. 4 is a view schematically illustrating a process of expanding fat cells by osmotic pressure of the hypotonic solution, and FIG. 5 is a view schematically illustrating a process of destroying fat cells by ultrasonic waves. FIG. 6 is a view schematically illustrating a process of discharging destroyed fat cells through blood vessels.

As illustrated in FIGS. 1 and 2, in a localized fat destroying method according to an exemplary embodiment of the present invention, a hypotonic solution is first prepared (S110). Here, the hypotonic solution 110 is a solution for allowing the inside to have a higher osmotic pressure than the outside with a semi-permeable membrane interposed therebetween, that is, a solution for allowing the inside to have a high concentration. For example, as illustrated in FIG. 2, the process of preparing the hypotonic solution 110 (S110) may include first preparing a saline solution which the same 0.9% NaCl solution as a isotonic solution, and adding distilled water so that the prepared saline solution becomes a 0.3 to 0.4% NaCl solution.

Therefore, as the hypotonic solution 110 becomes the 0.3 to 0.4% NaCl solution, by the osmotic pressure phenomenon, the expansion of fat cells 21 is maximally induced, while the expansion of a skin tissue 10 (a epidermis 11 and a dermis 12) may be prevented. For reference, as a result of animal experiments, it is confirmed that when the NaCl solution of the hypotonic solution 110 is less than 0.3%, the osmotic pressure phenomenon occurs extremely, and thus there are side effects such as expansion of the skin tissue as well as the fat cells, and it is confirmed that when the NaCl solution exceeds 0.4%, the occurrence degree of the osmotic pressure phenomenon is remarkably reduced.

In addition, the process of preparing the hypotonic solution 110 (S110) may further include a process of adding tanamin, which promotes blood and lymphatic circulation, aminophylline, which promotes lipolysis, and vitamin C that increases collagen synthesis to the saline solution.

Therefore, among subsequent processes (S120, S130, and S140), after the process of destroying the fat cells (see "21" of a left side of FIG. 5) with ultra waves is performing or completed, the fat cells destroyed with ultrasonic waves may be smoothly discharged through blood vessels B10 (that is, discharged by kidney and urine) without the coagulation due to the reaction of the tanamin and the aminophylline (see FIG. 6) and at the same time, the elasticity of the skin sagged by the destruction of the fat cells 21 may be increased by the action of vitamin C.

For example, in the process (S110) of preparing the hypotonic solution 110, the hypotonic solution 110 may comprise 53 to 63 wt % of distilled water, 2 to 3 wt % of aminophylline, 1 to 2 wt % of tanamin, 0.3 to 0.5 wt % of vitamin C, 1 to 3 wt % of a local anesthetic agent, lidocain, and a remaining content of a saline solution based on the weight ratio of the total composition. Each component will be described in detail as follows.

The distilled water is a factor for allowing the saline solution (0.9% isotonic saline solution) to be a 0.3 to 0.4% NaCl solution, and it can be seen that when the distilled water is less than 53 wt %, the NaCl solution of the hypotonic solution 110 exceeded 0.4%, and the occurrence degree of the osmotic pressure phenomenon is remarkably reduced. When the distilled water exceeds 63 wt %, the NaCl solution of the hypotonic solution 110 becomes less than 0.3%, and the osmotic pressure phenomenon occurs extremely, and not only the fat cells but also the skin tissue (injection site skin layer) are expanded to cause side effects such as redness or necrosis.

The aminophylline is a factor for promoting lipolysis. When aminophylline is less than 2 wt %, lipolysis is not promoted, and when the aminophylline exceeds 3 wt %, at least one of digestive symptoms (especially, nausea, vomiting, abdominal pain), neurological symptoms (headache, insomnia, anxiety, excitement, convulsions, etc.), circulatory system symptoms (tachycardia, ventricular arrhythmia) and musculoskeletal symptoms (rhabdomyolysis) may be rarely caused.

The tanamin is a factor for promoting blood and lymphatic circulation. When the tanamin is less than 1 wt %, the blood and lymphatic circulation is not promoted, and when the tanamin is more than 2 wt %, the efficacy is not increased, but the side effects such as skin irritation symptoms may be induced.

The vitamin C is a factor for increasing collagen synthesis. When the vitamin C is less than 0.3 wt %, it is difficult to obtain an effect of increasing cholanogen synthesis, and when the vitamin is more than 0.5 wt %, irritation symptoms (pain, redness, etc.) of an injection site may be induced.

The local anesthetic agent, lidocain, is a factor for preventing pain caused by stimulation of a drug after injection. When the lidocain is less than 1 wt %, a pain prevention effect is insignificant, and when the lidocain exceeded 3 wt %, side effects such as myocardial contraction abnormalities, arrhythmia, and convulsions may be rarely caused.

The saline solution is the same isotonic solution as a body fluid in the body, which is the remaining content of the hypotonic solution and is a 0.9% NaCl solution.

In addition, the hypotonic solution 110 may further include hyaluronidase in units of 1500 IU.

The hyaluronidase is known to hydrolyze the binding of hyaluronic acid (HA), D-glucuronic acid present in chondroitin and chondroitin sulfate, and N-acetyl-D-glucosamine as well known. The hyaluronidase may be accumulated in the dermis and perform depolymerization of the long-chain mucopolysaccharide, which is a cause of retardation by stay of the bound water and the capillary compression of the diffusion of the organic liquid, which removes metabolic waste.

The dypolymerization has been used as a method for removing of localized fat by cleaving a long chain of mucopolysaccharide into short chains, resulting in the lose of bound water and waste products and the recovery of intravenous and lymphatic circulation and achieving the lose of the local edema, injecting the hyaluronidase into the subcutaneous tissue to loosen the connective tissues in the abdomen to reduce tissue edema using the connective tissue dissolving action of the hyaluronidase, thereby helping blood and lymphatic circulation and smoothing the digestion and metabolism of fat cells in the abdomen. A lipidytic lymphatic drainage (LLD) therapy has been widely used as a method of removing localized fat by lipolysis using the hyaluronidase (Korean Patent Publication No. 10-2009-0111916).

Thereafter, as illustrated in FIGS. 1 and 3, the hypotonic solution 110 is injected into a local fat tissue 20 using a multi-needle 120 (S120). Here, the multi-needle 120 is an injection tool for simultaneously inserting a plurality of needles into the skin. Further, although not illustrated, the multi-needle 120 may have a structure in which the skin is tightly pulled by applying negative pressure to the skin so as to be deeply inserted into the skin.

Therefore, the hypotonic solution 110 may be simultaneously injected into the localized fat such as the abdomen or the side of the body through the multi-needle 120, and the osmotic pressure phenomenon through the hypotonic solution 110 may occur simultaneously in localized fat to significantly increase a fat destroying effect.

Thereafter, as illustrated in FIGS. 1 and 4, the hypotonic solution 110 injected into the fat tissue 20 is injected into the fat cells (see "21" in the left drawing of FIG. 4) by the osmotic pressure phenomenon to expand the fat cells (see "21" in the right drawing of FIG. 4) (S130). For reference, the osmotic pressure phenomenon is a phenomenon in which when two liquids with different concentrations are blocked with a semi-permeable membrane, a solvent is transferred from a lower concentration side to a higher concentration side of a solute.

Thus, when the hypotonic solution 110 is injected into the local fat tissue, the injected hypotonic solution 110 is injected into the fat cells 21 filled with a relatively high concentration of isotonic solution by the osmotic pressure phenomenon to expand the fat cells 21.

Particularly, when ultrasonic waves are applied to the fat cells 21 expanded by the hypotonic solution 110 as described later (see S140), a propagation speed is increased by about 3 times as compared with the fat cells which are not applied with the ultrasonic waves to greatly improve the destruction efficiency of the fat cells 21. Here, the fat cells 21 expanded by the hypotonic solution 110 may provide the same environment in which sound waves are transmitted in water. That is, the destruction efficiency of the fat cells 21 may be greatly increased as compared with a case where the hypotonic solution 110 is not injected but treated due to a characteristic of sound waves of which the propagation speed is increased by three times in water.

Then, as illustrated in FIGS. 1 and 5, the fat cells expanded by applying the ultrasound waves to the fat tissue 20 are destroyed with the ultrasonic waves (S140).

Therefore, while the fat cells 21 are expanded by the osmotic pressure phenomenon of the hypotonic solution 110 injected into the fat tissue 20 through the multi-needle 120, the expanded fat cells 21 are destroyed by applying the ultrasonic waves, so that local fat may be easily destroyed without damage to the skin such as existing frostbite by a non-invasive method.

Further, the process of destroying the fat cells with the ultrasonic waves (S140) may include a process of destroying the expanded fat cells or inducing destruction thereof by applying an impact caused by resonance to the expanded fat cells, and a process of destroying or dissolving the fat cells by applying high-intensity focused ultrasonic waves to the fat cells applied with the impact caused by resonance.

Accordingly, while a resonance effect is generated by the excitation of the ultrasonic waves oscillated in a cavitation ultrasound device (not illustrated), the fat cells (see "21" of the right drawing of FIG. 5) may be burst and destroyed by the impact caused by the resonance. In addition, in the high-intensity focused ultrasound device (not illustrated), while high heat is generated by the high-intensity focused ultrasound wave oscillated with the precise focus from the fat cells 21 as a target, the membranes of the fat cells 21 may be burst and destroyed or the fat cells 21 may be physically dissolved and destroyed by high heat. In addition, the elasticity of the skin 10 may be increased while the skin dermal layer 12 is stimulated by the heat effect of the high-intensity focused ultrasonic waves.

Hereinafter, a hypotonic solution for removing localized fat according to another embodiment of the present invention will be described.

A hypotonic solution for removing localized fat according to another embodiment of the present invention may comprise 53 to 63 wt % of distilled water, 2 to 3 wt % of aminophylline, 1 to 2 wt % of tanamin, 0.3 to 0.5 wt % of vitamin C, 1 to 3 wt % of a local anesthetic agent, lidocain, and a remaining content of a saline solution based on the weight ratio of the total composition.

Here, the description of each of the distilled water, the aminophylline, the tanamin, the vitamin C, the local anesthetic agent, lidocain, and the saline solution is mentioned in the process (S110) of preparing the hypotonic solution of an embodiment of the present invention, and therefore, a detailed description thereof will be omitted.

In addition, the hypotonic solution for removing localized fat according to another embodiment of the present invention may further include hyaluronidase in units of 1500 IU. The description of the hyaluronidase has been mentioned in the process (S110) of preparing the hypotonic solution of an embodiment of the present invention described above, and therefore, a detailed description thereof will be omitted here.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

| [Explanation of Reference Numerals and Symbols] | |
| --- | --- |
| 10: Skin tissue | 11: Epidermis |
| 12: Dermis | 20: Fat tissue |
| 21: Fat cell | 30: Muscle tissue |
| 110: Hypotonic solution | 120: Multi-needle |

The invention claimed is:

1. A localized fat destroying method comprising:
   preparing a hypotonic solution;
   injecting the hypotonic solution into a local fat tissue using a multi-needle;
   expanding fat cells while the hypotonic solution injected into the fat tissue is injected into the fat cells by an osmotic pressure phenomenon; and
   destroying the expanded fat cells by ultrasonic waves by applying the ultrasonic waves to the fat tissue,
   wherein in the preparing of the hypotonic solution, the hypotonic solution comprises 53 to 63 wt % of distilled water, 2 to 3 wt % of aminophylline, 1 to 2 wt % of tanamin, 0.3 to 0.5 wt % of vitamin C, and a remaining content of a saline solution based on the weight ratio of the total composition.

2. The localized fat destroying method of claim 1, wherein the destroying of the expanded fat cells by ultrasonic waves includes:
   destroying the expanded fat cells or inducing the destruction thereof by applying an impact caused by resonance to the expanded fat cells; and
   destroying or dissolving the fat cells by applying high-intensity focused ultrasonic waves to the fat cells applied with the impact caused by resonance.

3. The localized fat destroying method of claim 1, wherein the preparing of the hypotonic solution includes:
   preparing a saline solution which is a 0.9% NaCl solution equal to an isotonic solution; and
   adding distilled water so that the prepared saline solution is a 0.3 to 0.4% NaCl solution.

4. A hypotonic solution for removing localized fat comprising:
   53 to 63 wt % of distilled water, 2 to 3 wt % of aminophylline, 1 to 2 wt % of tanamin, 0.3 to 0.5 wt % of vitamin C, and a remaining content of a saline solution based on the weight ratio of the total composition.

\* \* \* \* \*